United States Patent [19]

Gangarosa et al.

[11] Patent Number: 4,985,678
[45] Date of Patent: Jan. 15, 1991

[54] HORIZONTAL FIELD IRON CORE MAGNETIC RESONANCE SCANNER

[75] Inventors: Raymond E. Gangarosa, Decatur, Ga.; K. Ming Chui, Chagrin Falls, Ohio

[73] Assignee: Picker International, Inc., Highland Heights, Ohio

[21] Appl. No.: 257,921

[22] Filed: Oct. 14, 1988

[51] Int. Cl.⁵ ............................................ G01R 33/20
[52] U.S. Cl. .................................. 324/318; 128/653.2; 335/296
[58] Field of Search ................ 324/318, 322, 307, 313; 128/653; 335/296, 297, 301

[56] References Cited

U.S. PATENT DOCUMENTS

| | | | |
|---|---|---|---|
| 2,962,636 | 11/1960 | Purcell | 317/158 |
| 4,359,706 | 11/1982 | Flack | 335/281 |
| 4,553,122 | 11/1985 | Young | 335/296 |
| 4,608,991 | 9/1986 | Rollwitz | 128/653 |
| 4,641,119 | 2/1987 | Moore | 335/297 |
| 4,644,313 | 2/1987 | Miyajima | 335/296 |
| 4,656,449 | 4/1987 | Mallard et al. | 324/318 |
| 4,673,882 | 6/1987 | Buford | 324/320 |
| 4,703,274 | 10/1987 | Kaufman et al. | 324/318 |
| 4,723,116 | 2/1988 | Mueller | 335/296 |
| 4,727,328 | 2/1988 | Carper et al. | 324/318 |
| 4,728,895 | 3/1988 | Briguet | 324/318 |
| 4,733,189 | 3/1988 | Punchard et al. | 324/318 |
| 4,737,716 | 4/1988 | Roemer et al. | 324/319 |
| 4,737,717 | 4/1988 | Petro | 324/320 |
| 4,771,785 | 9/1988 | Duer | 324/318 |
| 4,788,502 | 11/1988 | Keller et al. | 324/318 |
| 4,875,485 | 10/1989 | Matsutani | 324/318 |

Primary Examiner—Hezron E. Williams
Assistant Examiner—Louis M. Arana
Attorney, Agent, or Firm—Fay, Sharpe, Beall, Fagan, Minnich & McKee

[57] ABSTRACT

A patient is disposed on a patient couch (A) and positioned longitudinally and vertically to bring a region of interest within the patient into a gap between a pair of magnetic pole pieces (20, 22). Magnetic field driver(s) (50', 50, 52) generates a magnetic field through a U-shaped ferrous member (B) connected with the pole pieces and through the gap therebetween. The U-shaped ferrous member extends below the gap such that open access is provided to the patient from above. Shielding coils (62, 64, 66) are disposed between the U-shaped ferrous portion and the gap to compensate for distortion of the magnetic field in the gap attributable to magnetic flux through the U-shaped member. Magnetic resonance is excited in the region of interest of the patient between the pole pieces and magnetic resonance signals emanating therefrom are received, such as with a crossed elliptical quadrature coil (72). The received magnetic resonance signals are processed by processing circuitry (E) and image representations for display on a monitor (82).

19 Claims, 3 Drawing Sheets

HORIZONTAL FIELD IRON CORE MAGNETIC RESONANCE SCANNER

BACKGROUND OF THE INVENTION

The present invention relates to the art of generating magnetic fields, particularly, strong linear magnetic fields extending over relatively large distances. It finds particular application in conjunction with magnetic resonance imaging and will be described with particular reference thereto. However, it is to be appreciated that the present invention will also find application in conjunction with magnetic resonance spectroscopy, manufacturing materials with aligned dipoles, and the like.

Heretofore, most magnetic resonance imagers have generated the main or primary magnetic field axially through a plurality of annular magnetic coils. However, this air core design is relatively inefficient compared to an iron core magnet. Iron core magnets have well contained fringe fields, tend to be less costly to construct have improved patient access, have potential synergistic interaction between the pole faces and gradient coils, and have greater operational safety.

Others have heretofore constructed C or double-C-shaped iron core electromagnets for magnetic resonance applications. Even a relatively low field, e.g. 0.4 Tesla, magnet has a very large mass in the iron return path(s). In the prior art iron core magnets, the return path had not only a substantial cross section, but substantial overall length. In order to avoid distorting the magnetic field across the gap, the return path was positioned well away from the gap. That is, large C-shaped rather than shallow U-shaped return paths were utilized. The center point of the return path was disposed at a relatively large distance from the gap relative to the length of the gap in order to avoid distorting the magnetic field. The dual return paths of a double-C magnet tended to improve the symmetry or cancellation of distorting forces on the magnetic field.

As the field strength and gap distance increased, the cross section of the return path was also increased. The weight of the iron core increased approximately as the cube of the pole to pole spacing of the gap and linearly with the field strength. Due to this severe weight penalty, the gap of such magnets was minimized. To the extent such magnets were built for human imaging, the gaps were arranged vertically to accommodate the smallest front to back dimension of the human body.

The vertical gap iron core magnets had several drawbacks. First, the front to back dimension of the human body varied significantly from person to person. The gaps sized for the "average" person were too small and unusable for some persons. Further, when doing head scans, the patient was face to face with the upper pole creating a claustrophobic effect. The upper magnet also tended to interfere with range of motion studies, such as knee flexation studies.

The present invention contemplates a new and improved magnetic resonance apparatus and method which overcomes the above referenced problems and others.

SUMMARY OF THE INVENTION

In accordance with the present invention, a magnetic resonance imaging apparatus is provided. A patient support couch has a generally horizontal patient supporting surface, a longitudinal axis, and a transverse axis. An elevation adjusting means selectively adjusts the height of the patient supporting surface. A pair of magnetic pole pieces are disposed adjacent either side of the patient supporting surface for providing a horizontal magnetic field across a gap therebetween parallel to the transverse axis. A longitudinal adjustment means selectively adjusts the relative position of the pole pieces and the patient couch along the longitudinal axis. A ferrous path which interconnects the pole pieces is disposed principally below the patient support surface to provide open access to the patient from above. One or more magnetic field drivers generate a magnetic field along the ferrous path, hence, across the gap.

In the preferred embodiment, one or two drivers are placed in front of or at the pole faces. Alternatively, one or more drivers may be located at any position along the ferrous return path.

In accordance with another aspect of the present invention, a generally ferrous path is provided between a pair of horizontally spaced pole pieces. A magnetic field is induced in the ferrous path horizontally across the gap between the pole faces. A prone, supine, or seated patient is moved vertically and horizontally such that the magnetic path across the gap passes through a region of interest of the patient. Magnetic resonance is induced in the region of interest and magnetic resonance signals are received, processed, and reconstructed into an image representation. The U-shaped ferrous path provides ready access to the patient and the region of interest to facilitate various medical procedures.

A patient is positioned vertically and horizontally until a region of interest is disposed between a pair of pole pieces that define a horizontal gap therebetween of sufficient width to receive the patient's shoulders. A magnetic field is generated through a U-shaped ferrous member that connects the pole pieces, hence through the gap. Magnetic resonance signals from dipoles of the region of interest induced to resonance are received and processed to produce an image or other useful results.

In accordance with another aspect of the present invention, the method of magnetic resonance imaging is provided.

A primary advantage of the present invention is that the usable linear magnetic field is horizontally disposed along an axis parallel to the patient's shoulders. This facilitates a wide range of scanning procedures in which virtually any portion of the body can be imaged with improved coil geometries.

Another advantage of the present invention resides in the open space above the patient which facilitates range of motion studies and other procedures, invasive procedures, connection of life support equipment, and reduces patient claustrophobia.

Another advantage of the present invention resides in its ability to fit a wide range of patients.

Still further advantages of the present invention will become apparent to those of ordinary skill in the art upon reading and understanding the following detailed description of the preferred embodiments.

BRIEF DESCRIPTION OF THE DRAWINGS

The invention may take form in various parts and arrangements of parts. The drawings are only for purposes of illustrating preferred embodiments and are not to be construed as limiting the invention.

DETAILED DESCRIPTION OF THE PREFERRED EMBODIMENTS

Figure 1:
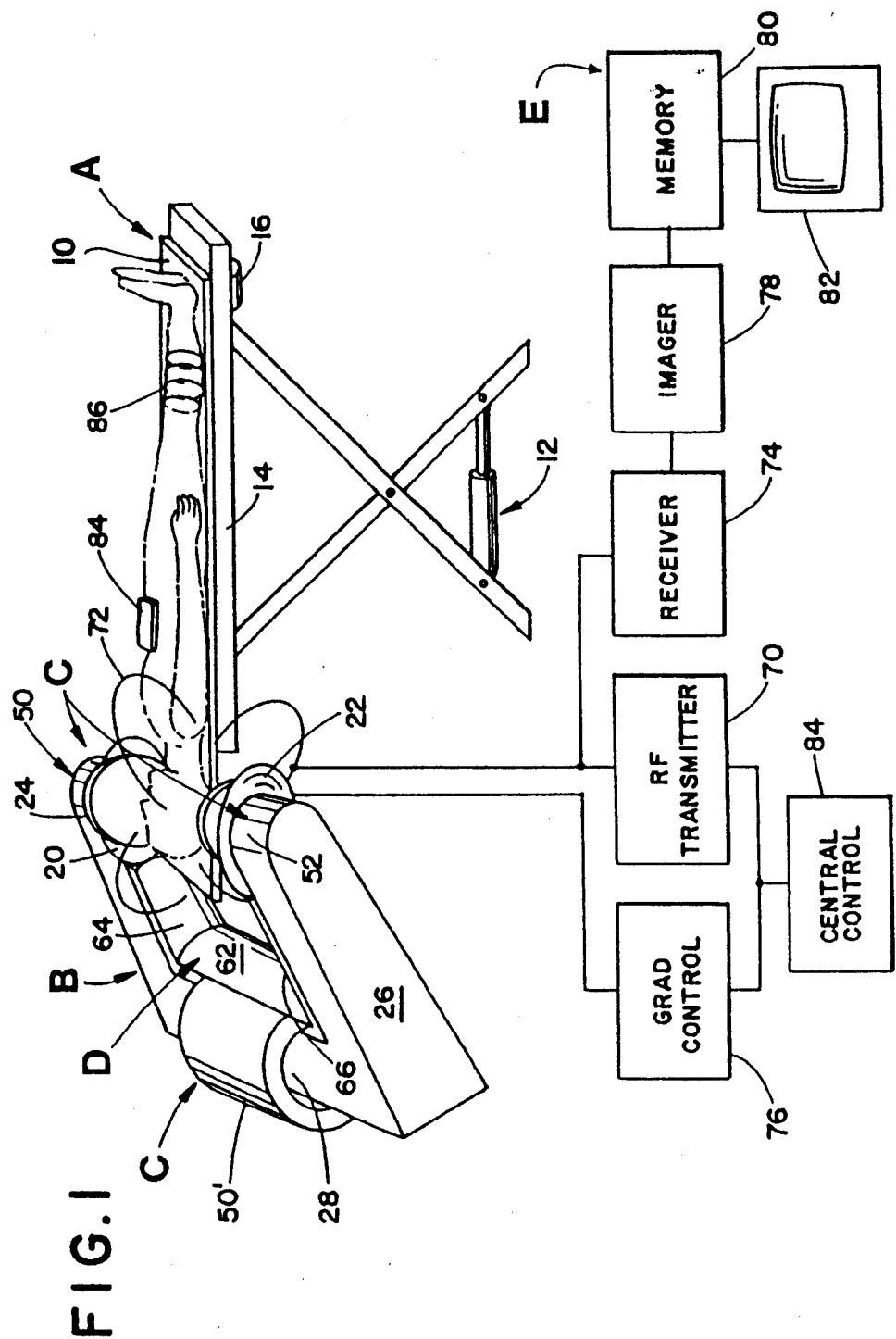
FIG. 1 is a diagrammatic illustration of a magnetic resonance imaging apparatus in accordance with the present invention.

A patient couch A selectively supports a patient or subject in an air gap defined between pole faces of a U-shaped iron or ferrous return path B. A magnetomotive force means C creates a magnetic field across the air gap between the pole faces and along the ferrous path B. A correction field means D neutralizes distortion of the air gap magnetic field attributable to at least portions of the ferrous path B. Magnetic resonance electronics E selectively induce magnetic resonance of dipoles in the image region and processing resultant received magnetic resonance signals to create an image or other diagnostic information.

The patient couch A includes a patient supporting surface 10 in a substantially horizontal plane. The patient supporting surface has a longitudinal axis lengthwise therealong and a perpendicular transverse axis thereacross, both in the horizontal plane. An elevation adjusting means 12 selectively adjusts the relative height of the patient supporting surface and the gap. The patient supporting surface 10 is slidably mounted on a support frame 14 to provide a means for moving the patient supporting surface and the pole faces relative to each other along the longitudinal axis. Preferably, a motor drive 16 is mounted to the frame 14 to drive the patient supporting surface therealong.

The ferrous path B connects a first pole piece 20 and a second pole piece 22 which define the air gap therebetween. The ferrous path includes first and second side portions 24, 26 and a connecting portion 28. The side and connecting portions are configured so as to minimize the length of the ferrous path which minimizes its substantial weight. The side portions extend directly rearward from the pole pieces without bowing outward along a C-shaped path to minimize the length. The side pieces extend parallel but could converge. This forms a U-shaped rather than C-shaped return path. The magnet may be tilted at an angle for optimal space utilization.

Figure 2:
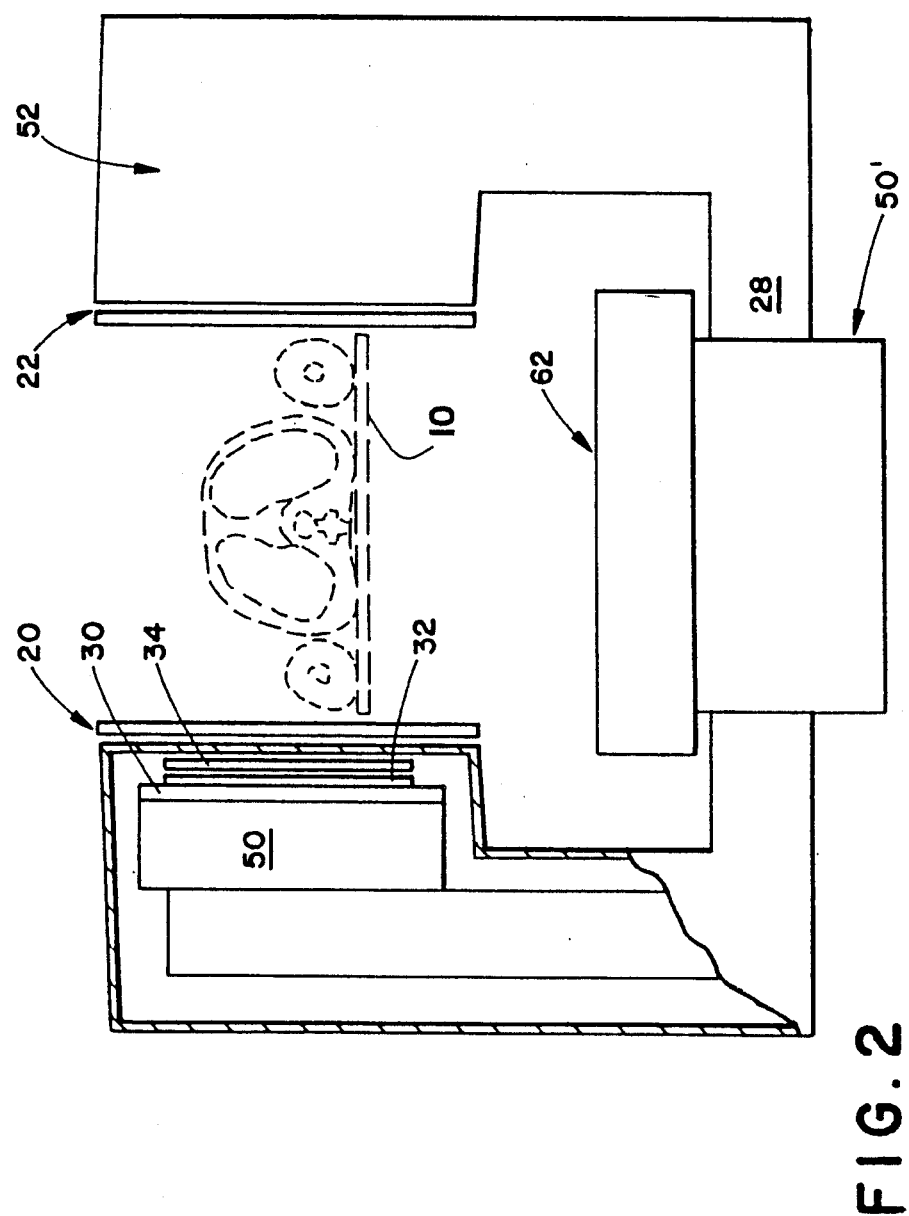
FIG. 2 is a cross sectional view illustrating gradient coil details of the apparatus of FIG. 1.

With reference to FIG. 2, the pole pieces 20 and 22 each include a soft ferrite or laminated pole face 30 configured to suppress eddy currents and passive and/or active shim coils 32. The active shim coil is iteratively adjusted until the magnetic field between the pole pieces is optimized. Preferably, the field's uniformity is maximized. Although in some applications it may be preferable to create selected non-uniformities, e.g. create non-uniformities that remove breathing artifacts or other moving tissue from the resultant image. The shimming also compensates for edge effects, pole face irregularities, the influence of adjoining equipment, and the like. A gradient field coil 34 selectively produces gradients across the magnetic field. More specifically, the gradient coil preferably includes appropriate coil segments to create gradients in either the vertical or longitudinal directions across the magnetic field in the air gap.

Figure 3A:
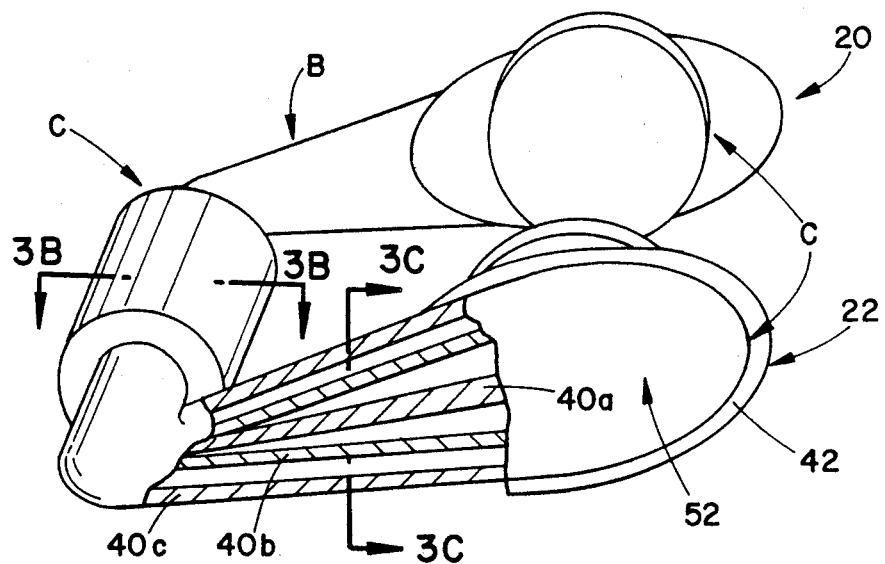
FIGS. 3A, 3B, 3C, and 3D illustrate alternate embodiments of a ferrous return path, a cross section therethrough the cryo driver(s), a cross section through the side arm, and pole piece construction, respectively; and, FIGS. 4A and 4B illustrate magnetic field correction structures with transverse and axial corrective coils, respectively.
Figure 3B:
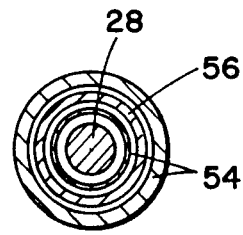
Figure 3C:
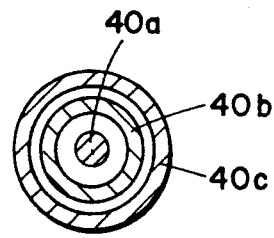
Figure 3D:
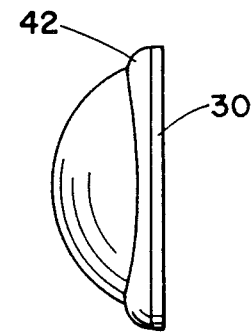

With references to FIGS. 3A, 3B, 3C and 3D, the ferrous return path may be solid, laminated, include an air core or the like. In the embodiment of FIGS. 3A-C, the return path has concentric ferrous tubes 40a, 40b, 40c with annular air gaps therebetween. The tubes flare outward toward the pole faces to provide a smooth transition between the solid core through the magnetomotive force means C and the larger cross section pole pieces which may be circular, oval, or rectangular. The return path connects to an unsaturated plate 42 of the pole pieces which is connected with the soft ferrite or laminated pole face 30 to control hysteresis. In the preferred embodiment, the pole faces are ellipses with their long axis parallel to the longitudinal axis and with their short axis in the vertical direction. In this manner, the cross section of the pole face mimics the aspect ratio of the patient. This enables the imaging region to be extended along the length of the patient even although shortened along the front to back dimension of the patient. However, because the patient may be freely moved in the vertical direction, the patient can be raised and lowered to align the physiological structure of interest with the air gap magnetic field.

The magnetomotive force means C, in the preferred embodiment, includes cryodrivers 50, 52 disposed adjacent the pole pieces 20, 22. Each cryodriver includes a dewar 54 which holds superconducting coils 56 that wrap annularly around the magnetic flux path. The dewar further holds a refrigerant, such as liquid helium, around the superconducting coils to hold them at a temperature which is within their superconducting range. Alternately or additionally, a cryodriver 50' may encircle a segment of the connecting portion 28. Optionally, other magnetic force generating arrangements, such as resistance coils or permanent magnets, can be utilized.

Figure 4A:
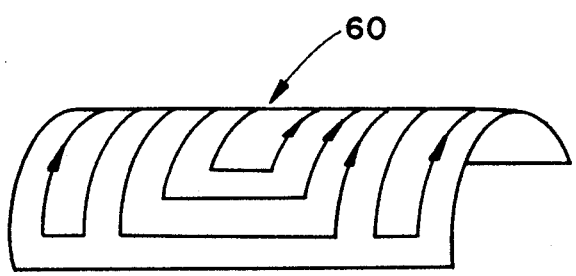
Figure 4B:
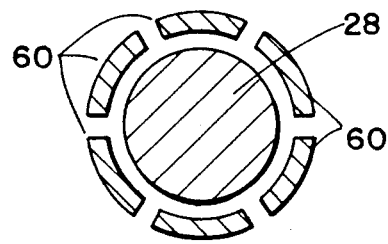

With reference to FIGS. 4A and 4B and continuing reference to FIG. 1, the corrective field means D includes a plurality of active coils, i.e. radial or axial, 62, 64, and 66. The coils include a plurality of loops and current paths. The exact coil pattern and current densities through the current coil path are selected individually for each magnet. More specifically, the coils and current densities are selected such that the correction coils generate a magnetic field which substantially cancels, i.e. is equal and opposite to, the magnetic fields generated by the ferrous path.

More specifically, the corrective field coils include a first or central coil array 62 and a pair of side coil arrays 64, 66. The central coil array primarily counteracts the magnetic effect of the connecting portion 28 and the cryodrivers 50', 50, 52. The side coil portions 64 and 66 primarily counteract the effects of magnetic fields generated by the side ferrous portions 24, 26. The exact configuration of the central and side coils is preferably determined by computer modeling. The configuration of the pole pieces is selected and optimized for the desired application. In the preferred embodiment, one or two magnetic drivers 50, 52 are placed at or near the pole faces. If the cryodriver is further displaced from the magnetic field gap along the ferrous path B, e.g. cryodriver 50', there is greater magnetic leakage requiring a larger driver, hence, more weight. Appropriate correction coils and modifications to the pole faces, such as tilting pole faces, are computer simulated until the ferrous path is rendered substantially invisible to the gap magnetic field. If the ferrous path is symmetric, the correction is simpler.

The ferrous path is then redefined to move the magnetic driver closer, i.e. shorten the sides. This again causes magnetic field distortion and shunting. The design of the coils and correction coil current flux is modified to compensate. Of course, shortening the ferrous path allows its cross section to be reduced to achieve a two fold weight reduction. The process is repeated iteratively until an optimum balanced between return path weight and gap field linearity is achieved.

In the preferred embodiment, the correction coils, like the magnetic driver coils are superconducting and housed in a cryogenic vessel. If the correction coils are remotely adjustable, greater latitude in shimming of the actually constructed physical magnet is accommodated. A set of superconductive shims may be provided for this purpose. With the reduction of iron in the ferrous return path, it may be economically feasible to use a more expensive, higher permeability material. Such higher permeability may also help compensate for saturation of the return path attributable to the correction coils.

The electronics E include an RF transmitter means 70 which selectively applies radio frequency pulses to a crossed ellipse quadrature coil 72 to excite magnetic resonance of dipoles in the gap magnetic field. A receiver 74 receives magnetic resonance signals from the region of interest using the coil as an antenna. A gradient coil control means 76 applies electrical pulses to the gradient field coils 34 to cause gradients across the gap magnetic field to encode the magnetic resonance signals. An image reconstruction means 78 performs an inverse two dimensional Fourier transform or other known algorithm to reconstruct an image representation from the received magnetic resonance signals. The image representations may be stored in a memory 80, displayed on a video monitor 82, further processed, or the like. A central magnetic resonance controller 84 controls the RF transmitter 70, and the gradient field control means 76 to implement a preselected magnetic resonance imaging sequence as is conventional in the art.

Rather than using the same coil for transmission and reception, surface coils such as a coil loop 84 or solenoid coil 86 may be disposed in the image region and used to receive the magnetic resonance signals. Further, rather than crossed ellipse quadrature coils, other coil arrangements may be utilized, such as saddle quadrature coils, solenoid coils, saddle coils, butterfly coils, or phased array coils.

The invention has been described with reference to the preferred embodiments. Obviously, modifications and alterations will occur to others upon reading and understanding the preceding detailed description of the preferred embodiment. It is intended that the invention be construed as including all such alterations and modifications insofar as they come within the scope of the appended claims or the equivalents thereof.

Having thus described the preferred embodiment, the invention is now claimed to be:

1. A magnetic resonance imaging apparatus comprising:
   a patient supporting couch having a generally horizontal patient supporting surface, a longitudinal axis, and a transverse axis, whereby a patient is disposable on the patient supporting surface with its head and feet along the longitudinal axis and shoulders along the transverse axis;
   a pair of pole pieces disposed adjacent opposite sides of the patient supporting surface for providing an air gap therebetween parallel to the transverse axis;
   an adjusting means for adjusting a relative position of the patient supporting surface and the pole pieces;
   a ferrous member interconnecting the pole pieces, the ferrous member being disposed principally below the patient supporting surface such that the patient is able to be moved freely between the pole pieces and substantial clearance is provided above the patient, the ferrous member including a pair of side members extending from the pole pieces generally parallel to each other and a connecting member connecting the side members together below the patient supporting surface, the ferrous member side portions each including a plurality of tubular, concentric ferrous members having air gaps therebetween;
   at least one magnetic field driver disposed for generating a magnetic field through the ferrous member and through the air gap defined between the pole pieces parallel to the transverse axis;
   a receiving coil disposed adjacent the pole pieces for receiving magnetic resonance signals from resonating dipoles in the gap between the pole pieces; and,
   electronic circuitry for processing the magnetic resonance signals received by the receiver coil into an image representation.

2. The apparatus as set forth in claim 1 wherein the pole pieces are elongated parallel to the longitudinal axis.

3. The apparatus as set forth in claim 1 wherein the receiving coil is a saddle coil.

4. The apparatus as set forth in claim 1 wherein the receiving coil is a solenoid coil.

5. The apparatus as set forth in claim 1 wherein the receiving coil is a quadrature coil.

6. The apparatus as set forth in claim 1 wherein the receiving coil is a phased array coil.

7. The apparatus as set forth in claim 1 further including a radio frequency transmitting means for transmitting radio frequency signals to the receiving coil for inducing the magnetic resonance.

8. The apparatus as set forth in claim 1 wherein the at least one magnetic field driver includes a coil arrangement mounted adjacent the pole faces.

9. A magnetic resonance imaging apparatus comprising:
   a patient supporting couch having a generally horizontal patient supporting surface, a longitudinal axis, and a transverse axis, whereby a patient is disposable on the patient supporting surface with its head and feet along the longitudinal axis and shoulders along the transverse axis;
   a pair of pole pieces disposed adjacent opposite sides of the patient supporting surface for providing a primary magnetic field air gap therebetween parallel to the transverse axis;
   an adjusting means for adjusting a relative position of the patient supporting surface and the pole pieces;
   a ferrous member interconnecting the pole pieces, the ferrous member being disposed principally below the patient supporting surface such that the patient is able to be moved freely between the pole pieces and substantial clearance is provided above the patient, the ferrous member including a pair of side members extending from the pole pieces generally parallel to each other and a connecting member that conencts the side members below the patient supporting surface;

a magnetic field driver connected with the connecting member for generating a magnetic flux loop through the connecting member, the side members, and the pole pieces to create a primary magnetic field across the air gap generally parallel to the transverse axis, the magnetic flux driver and the connecting member causing a secondary magnetic field in the air gap that bends the primary magnetic field out of parallel to the transverse axis;

shimming coils disposed contiguous to the pole pieces for optimizing uniformity of the primary magnetic field in the air gap;

a magnetic field correcting means disposed between at least the ferrous member connecting portion and the air gap for shielding the primary magnetic field from the effects of the secondary magnetic fields, whereby magnetic field bending caused by the cross member and magnetic field driver are rendered substantially invisible to the primary magnetic field in the gap;

gradient field coils for creating gradients in the primary magnetic field in the gap;

a coil assembly disposed adjacent the pole pieces for at least one of (i) transmitting radio frequency signals into the gap to induce resonance and (ii) receiving magnetic resonance signals emanating from resonating dipoles in the gap; and, electronic circuitry for processing the magnetic resonance signals received by the receiver coil into an image representation.

10. The magnetic resonance imaging apparatus as set forth in claim 9 wherein the magnetic field driver includes:

a dewar and at least one superconducting coil surrounding the cross portion to generate the magnetic flux through the ferrous member.

11. A method of magnetic resonance imaging comprising:

providing a pair of pole pieces which define an air gap horizontally therebetween of sufficient width for passing shoulders of a patient therethrough;

providing a magnetic flux return path through a ferrous member which connects the pole pieces, the magnetic flux return path extending generally downward from the pole pieces to pass below a patient when portions of a horizontally disposed patient are positioned between the pole pieces to provide open access to the patient from above;

positioning the patient vertically and longitudinally until a selected portion of the patient is disposed between the pole pieces;

generating magnetic flux through the ferrous member and a primary magnetic field through the air gap between the pole pieces and the patient portion disposed therein, the flux through the ferrous member generating a secondary magnetic field in the air which warps the primary magnetic field;

shielding the primary magnetic field from the secondary magnetic field, whereby the ferrous member may be disposed close to the air gap without distorting the primary magnetic field;

inducing dipoles of the patient portion in the air gap to magnetic resonance;

receiving magnetic resonance signals from the resonating dipoles; and, processing the received magnetic resonance signals to generate a magnetic resonance image or the like.

12. The method as set forth in claim 11 wherein the step of receiving magnetic resonance signals includes detecting the magnetic resonance signals with a crossed ellipse coil disposed at least partially in the gap between the pole pieces.

13. The method as set forth in claim 11 wherein the step of inducing magnetic resonance includes providing radio frequency pulses to a crossed ellipse coil disposed at least partially in the gap between the pole faces.

14. The method as set forth in claim 13 wherein the step of receiving magnetic resonance signals includes detecting magnetic resonance signals with the crossed ellipse coil.

15. The method as set forth in claim 13 wherein the step of receiving magnetic resonance signals includes receiving magnetic resonance signals with a solenoid coil disposed at least partially in the gap between the pole pieces.

16. The method as set forth in claim 13 wherein the step of receiving magnetic resonance signals includes detecting magnetic resonance signals with a surface coil disposed at least partially in the gap between the pole pieces.

17. The method as set forth in claim 11 wherein the step of providing pole pieces includes providing pole pieces with a major axis and a minor axis, orienting the pole piece major axis horizontally along a longitudinal axis of the patient positioned between the pole pieces, whereby the air gap magnetic field is elongated along the length of the patient.

18. The method as set forth in claim 11 wherein magnetic resonance signals for generating a plurality of magnetic resonance images are collected as the patient progressively bends a joint disposed in the air gap from image to image to perform a range of motion study.

19. A magnetic resonance imaging apparatus:

a patient supporting couch having a generally horizontal patient supporting surface, a longitudinal axis, and a transverse axis;

a pair of elliptical pole pieces disposed adjacent opposite sides of the patient supporting surface, the pole pieces each having a major axis oriented horizontally along the patient supporting surface parallel to the longitudinal axis and a minor axis disposed vertically transverse to the longitudinal and transverse axes, such that a magnetic field generated between poles is elongated along the longitudinal axis of the patient supporting surface;

an adjusting means for adjusting the patient supporting surface relative to the pole pieces;

a U-shaped ferrous member including side portions each connected to one of the pole pieces and a connecting portion which connects the side portions, the connecting portion being disposed below the patient supporting surface;

a magnetic field driver disposed below the patient supporting surface adjacent the cross portion for generating magnetic flux through the U-shaped ferrous member and creating the magnetic field in the air gap between the elliptical pole pieces;

a pair of shimming coil assemblies, each shimming coil assembly disposed contiguous to one of the pole pieces for optimizing the magnetic field therebetween;

gradient field coils mounted to the pole pieces for creating gradients in the magnetic field between the pole faces;

a coil assembly mounted at least partially in the horizontal gap for transmitting radio frequency signals into the gap to induce magnetic resonance of dipoles disposed in the gap and for receiving magnetic resonance signals emanating from resonating dipoles in the horizontal gap; and, electronic circuitry for processing the received magnetic resonance signals into an image representation.

* * * * *